(12) United States Patent (10) Patent No.: US 7,922,728 B2
Tornier et al. (45) Date of Patent: Apr. 12, 2011

(54) ANCILLARY TOOL FOR FITTING AN ULNAR COMPONENT AND/OR A RADIAL COMPONENT OF AN ELBOW PROSTHESIS

(75) Inventors: Alain Tornier, Saint Ismier (FR); Shawn O'Driscoll, Rochester, MN (US); Graham King, London (CA); Ken Yamaguchi, Saint Louis, MO (US); Yves Alain Ratron, Grenobie (FR); Bruno Scialom, Gieres (FR)

(73) Assignee: Tornier SAS, Saint Ismier (FR)

( * ) Notice: Subject to any disclaimer, the term of this patent is extended or adjusted under 35 U.S.C. 154(b) by 1112 days.

(21) Appl. No.: 10/189,378

(22) Filed: Jul. 8, 2002

(65) Prior Publication Data

US 2003/0009170 A1 Jan. 9, 2003

Related U.S. Application Data

(60) Provisional application No. 60/303,321, filed on Jul. 9, 2001.

(51) Int. Cl.
*A61F 5/00* (2006.01)
(52) U.S. Cl. .................................... 606/87; 606/86 R
(58) Field of Classification Search ............. 606/86, 606/87–90, 99, 86 R; 623/18.11, 19.11–19.14, 623/20.11–20.13
See application file for complete search history.

(56) References Cited

U.S. PATENT DOCUMENTS

| | | | | |
|---|---|---|---|---|
| 4,131,956 A | * | 1/1979 | Treace | 623/20.11 |
| 4,242,758 A | | 1/1981 | Amis et al. | |
| 4,257,411 A | * | 3/1981 | Cho | 606/96 |
| 4,378,607 A | * | 4/1983 | Wadsworth | 623/20.11 |
| 4,383,337 A | | 5/1983 | Volz et al. | |
| 4,538,306 A | | 9/1985 | Dorre et al. | |
| 4,686,978 A | * | 8/1987 | Wadsworth | 606/84 |
| 4,718,414 A | | 1/1988 | Saunders et al. | |
| 4,721,104 A | * | 1/1988 | Kaufman et al. | 606/88 |
| 4,822,364 A | | 4/1989 | Inglis et al. | |
| 4,892,546 A | | 1/1990 | Kotz et al. | |
| 4,893,619 A | * | 1/1990 | Dale et al. | 606/87 |
| 5,021,055 A | * | 6/1991 | Burkinshaw et al. | 606/82 |
| 5,042,983 A | * | 8/1991 | Rayhack | 606/87 |

(Continued)

FOREIGN PATENT DOCUMENTS

DE 19512854 8/1996

(Continued)

OTHER PUBLICATIONS

Rochetin, U.S. Appl. No. 11/194,452, entitled "Patellar Retractor and Method of Surgical Procedure on Knee," filed Aug. 2, 2005.

(Continued)

*Primary Examiner* — Thomas C Barrett
*Assistant Examiner* — Andrew Yang
(74) *Attorney, Agent, or Firm* — Faegre & Benson LLP (57) ABSTRACT

An ancillary tool (10) comprising a trial humeral trochlea ($20_2$) that is representative of an anatomical humeral trochlea when the trial humeral trochlea is in place with respect to corresponding cubital ($S_C$) and/or radial ($S_R$) articular surfaces and a cut-out guide (30) for cutting an ulna (C) and/or a radius (R), wherein the cut-out guide (30) is adapted to be positioned with respect to the trial humeral trochlea ($20_2$). The cut-out guide (30) is also adapted to be positioned with respect to an ulna (C) and/or to a radius (R) equipped with the trial humeral trochlea ($20_2$).

25 Claims, 6 Drawing Sheets

U.S. PATENT DOCUMENTS

| | | | | |
|---|---|---|---|---|
| 5,100,407 A | * | 3/1992 | Conrad et al. | 606/79 |
| 5,133,761 A | | 7/1992 | Krouskop | |
| 5,171,289 A | | 12/1992 | Tornier | |
| 5,314,484 A | | 5/1994 | Huene | |
| 5,314,485 A | * | 5/1994 | Judet | 623/21.13 |
| 5,326,359 A | | 7/1994 | Oudard | |
| 5,358,526 A | | 10/1994 | Tornier | |
| 5,364,401 A | * | 11/1994 | Ferrante et al. | 606/84 |
| 5,405,399 A | | 4/1995 | Tornier | |
| 5,429,639 A | | 7/1995 | Judet | |
| 5,458,650 A | | 10/1995 | Carret et al. | |
| 5,505,731 A | | 4/1996 | Tornier | |
| 5,540,697 A | * | 7/1996 | Rehmann et al. | 606/91 |
| 5,591,168 A | | 1/1997 | Judet et al. | |
| 5,628,749 A | * | 5/1997 | Vendrely et al. | 606/80 |
| 5,645,548 A | * | 7/1997 | Augsburger | 606/87 |
| 5,649,930 A | * | 7/1997 | Kertzner | 606/96 |
| 5,662,651 A | | 9/1997 | Tornier et al. | |
| 5,662,656 A | * | 9/1997 | White | 606/88 |
| 5,676,702 A | | 10/1997 | Ratron | |
| 5,681,316 A | * | 10/1997 | DeOrio et al. | 606/88 |
| 5,702,447 A | | 12/1997 | Walch et al. | |
| 5,702,457 A | * | 12/1997 | Walch et al. | 623/19.13 |
| 5,702,470 A | * | 12/1997 | Menon | 623/21.12 |
| 5,702,471 A | | 12/1997 | Grundei et al. | |
| 5,702,478 A | | 12/1997 | Tornier | |
| 5,723,015 A | | 3/1998 | Risung et al. | |
| 5,746,771 A | * | 5/1998 | Clement et al. | 623/23.22 |
| 5,766,256 A | | 6/1998 | Oudard et al. | |
| 5,779,709 A | * | 7/1998 | Harris et al. | 606/87 |
| 5,824,106 A | | 10/1998 | Foumol | |
| 5,879,395 A | | 3/1999 | Tornier et al. | |
| 5,916,219 A | * | 6/1999 | Matsuno et al. | 606/88 |
| 5,941,884 A | * | 8/1999 | Corvelli et al. | 606/88 |
| 6,027,534 A | | 2/2000 | Wack et al. | |
| 6,059,832 A | * | 5/2000 | Menon | 623/21.15 |
| 6,162,254 A | | 12/2000 | Timoteo | |
| 6,165,224 A | | 12/2000 | Tornier | |
| 6,168,629 B1 | | 1/2001 | Timoteo | |
| 6,171,341 B1 | | 1/2001 | Boileau et al. | |
| 6,183,519 B1 | | 2/2001 | Bonnin et al. | |
| 6,206,925 B1 | | 3/2001 | Tornier | |
| 6,290,725 B1 | | 9/2001 | Weiss et al. | |
| 6,299,646 B1 | | 10/2001 | Chambat et al. | |
| 6,328,758 B1 | | 12/2001 | Tornier et al. | |
| 6,334,874 B1 | | 1/2002 | Tornier et al. | |
| 6,379,387 B1 | | 4/2002 | Tornier | |
| 6,454,809 B1 | | 9/2002 | Tornier | |
| 6,488,712 B1 | | 12/2002 | Tornier et al. | |
| 6,494,913 B1 | * | 12/2002 | Huebner | 623/19.11 |
| 6,540,770 B1 | | 4/2003 | Tornier et al. | |
| 6,582,469 B1 | | 6/2003 | Tornier | |
| 6,599,295 B1 | | 7/2003 | Tornier et al. | |
| 6,626,946 B1 | | 9/2003 | Walch et al. | |
| 6,699,290 B1 | * | 3/2004 | Wack et al. | 623/20.12 |
| 6,761,740 B2 | | 7/2004 | Tornier | |
| 6,767,368 B2 | | 7/2004 | Tornier | |
| 6,802,864 B2 | | 10/2004 | Tornier | |
| 6,824,567 B2 | | 11/2004 | Tornier et al. | |
| 6,890,357 B2 | * | 5/2005 | Tornier | 623/20.12 |
| 6,945,976 B2 | * | 9/2005 | Ball et al. | 606/87 |
| 6,969,406 B2 | | 11/2005 | Tornier | |
| 7,033,396 B2 | | 4/2006 | Tornier | |
| 2002/0165614 A1 | * | 11/2002 | Tornier | 623/20.12 |
| 2003/0009171 A1 | | 1/2003 | Tornier | |
| 2003/0028198 A1 | | 2/2003 | Tornier et al. | |
| 2003/0149486 A1 | * | 8/2003 | Huebner | 623/19.11 |
| 2003/0208276 A1 | * | 11/2003 | Berelsman et al. | 623/20.11 |
| 2003/0208277 A1 | * | 11/2003 | Weiss et al. | 623/20.12 |
| 2004/0134821 A1 | | 7/2004 | Tornier | |
| 2004/0210220 A1 | | 10/2004 | Tornier | |
| 2004/0215200 A1 | | 10/2004 | Tornier et al. | |
| 2004/0230197 A1 | | 11/2004 | Tornier et al. | |
| 2005/0049709 A1 | | 3/2005 | Tornier | |
| 2005/0055102 A1 | | 3/2005 | Tornier et al. | |
| 2005/0165490 A1 | | 7/2005 | Tornier | |
| 2005/0203536 A1 | | 9/2005 | Laffargue et al. | |
| 2005/0278030 A1 | | 12/2005 | Tornier et al. | |
| 2005/0278031 A1 | | 12/2005 | Tornier et al. | |
| 2005/0278032 A1 | | 12/2005 | Tornier et al. | |
| 2005/0278033 A1 | | 12/2005 | Tornier et al. | |
| 2005/0288791 A1 | | 12/2005 | Tornier et al. | |
| 2006/0015185 A1 | | 1/2006 | Chambat et al. | |
| 2006/0173457 A1 | | 8/2006 | Tornier | |
| 2006/0173546 A1 | * | 8/2006 | Berelsman et al. | 623/20.11 |
| 2006/0235538 A1 | | 10/2006 | Rochetin et al. | |

FOREIGN PATENT DOCUMENTS

| | | |
|---|---|---|
| EP | 0006314 | 1/1980 |
| EP | 0098466 | 1/1984 |
| EP | 0132284 | 1/1985 |
| EP | 0913133 | 5/1999 |
| EP | 1051954 | 11/2000 |
| FR | 2663838 | 1/1992 |
| GB | 1537479 | 12/1978 |

OTHER PUBLICATIONS

Rochetin et al., U.S. Appl. No. 11/401,415, entitled "Surgical Apparatus for Implantation of a Partial or Total Knee Prosthesis," filed Apr. 11, 2006.

Rochetin, U.S. Appl. No. 11/670,274, entitled "Offset Stem Tibial Implantation," filed Feb. 1, 2007.

Ratron et al., U.S. Appl. No. 11/626,735, entitled "Surgical Instrumentation Kit for Inserting an Ankle Prothesis," filed Jan. 24, 2007.

* cited by examiner

ANCILLARY TOOL FOR FITTING AN ULNAR COMPONENT AND/OR A RADIAL COMPONENT OF AN ELBOW PROSTHESIS

CROSS REFERENCE TO RELATED APPLICATION

This application claims the benefit of U.S. Provisional Patent Application Ser. No. 60/303,321 filed on Jul. 9, 2001 by the same inventor, Alain Tornier.

FIELD OF THE INVENTION

The invention relates to an ancillary device for fitting an ulnar component and/or a radial component of a total or partial elbow prosthesis.

BACKGROUND OF THE INVENTION

An elbow prosthesis, such as known from EP-A-1 051 954, comprises an ulnar component and a radial component which must reproduce the ulnar and radial articular surfaces. The positioning of these surfaces with respect to the joint, particularly with respect to the humeral trochlea, is essential for the elbow thus fitted out to function well.

Up to the present time, surgeons implant the ulnar and radial components of elbow prostheses after dislocating the joint and attempting to reproduce the anatomical configuration of ulnar and radial articular surfaces. However, such reproduction is not perfect, hence a poor cooperation of the ulnar and/or radial articular surfaces with the humeral trochlea. This leads to premature wear of these surfaces and to discomfort for patients.

It is a particular object of the invention to overcome these drawbacks by proposing an ancillary fitting tool which allows precise positioning of the ulnar component and/or of the radial component with respect to the humeral trochlea, which substantially improves the functional conditions of the elbow thus fitted out.

SUMMARY OF THE INVENTION

Accordingly, the invention relates to an ancillary tool for fitting an ulnar component and/or a radial component of a total or partial elbow prosthesis, which comprises a trial humeral trochlea that is representative of an anatomical humeral trochlea when the trial humeral trochlea is in place with respect to corresponding ulnar and/or radial articular surfaces and a cut-out guide for cutting an ulna and/or a radius, wherein the guide is adapted to be positioned with respect to the trial humeral trochlea. The cut-out guide is also adapted to be positioned with respect to an ulna and/or a radius equipped with the trial humeral trochlea.

As a result of the invention, the guide enables the surgeon to mark the zones of resection of the bone or bones, taking into account the real dimensions of the trochlea. In other words, the cut-out guide functions like a three-dimensional anatomical sensor of the surface of the trochea, which allows the zones of cut to be efficiently positioned with respect to this trochlea.

According to advantageous but non-obligatory aspects of the invention, the ancillary tool incorporates one or more of the following characteristics:

The guide comprises a support on which the trial trochlea may be mounted and on which are mounted screws adapted to bear against the ulna and/or the radius for immobilization of the guide with respect to these bones.

The aforementioned support extends in a rod adapted to be positioned, over the major part of its length, parallel to a patient's forearm. This rod allows the surgeon to rapidly pre-position the support before a fine adjustment obtained due to the aforementioned screws.

The aforementioned support forms a cylindrical member for guiding a bell-shaped saw for the preparation of the upper end of the ulna.

The aforementioned support comprises a tab which supports a shaft on which the trial trochlea may be mounted. In that case, the axes of symmetry of the cylindrical member for guiding the bell-shaped saw and of the shaft on which the trial trochlea may be mounted, are advantageously merged, the aforementioned shaft being hollow and forming a volume for slide and guiding of a central pin of the bell-shaped saw.

The afore-mentioned support extends in a rod adapted to be positioned, over the major part of its length, parallel to the patient's fore-arm. This rod allows the surgeon to rapidly pre-position the support before a fine adjustment obtained thanks to the aforementioned screws.

The support is formed by assembling a plurality of pieces selected as a function of the size of the trial trochlea. In other words, the geometry of the support depends on the size of the trial trochlea, i.e. in fact on the size of the anatomical trochlea of which the trial trochlea is a three-dimensional representation. This adaptation to the size of the anatomical trochlea allows a corresponding adaptation of the ulnar and radial cut-out zones.

A guiding tool is provided for boring the ulna, this tool comprising a template adapted to abut against the cut-out surface of the olecranon, this template being provided with a bore for guiding a drill or the like, while this template is fast with a handle for adjusting its angular position with respect to a central axis of the cut-out surface.

The invention allows an ulnar component or a radial component of an elbow prosthesis to be fitted in accordance with a method which comprises: positioning a cut-out guide with respect to a trial humeral trochlea representative of the anatomical humeral trochlea, when the trial trochlea is in place with respect to the corresponding ulnar and/or radial articular surfaces, immobilizing this guide with respect to the ulna and/or radius, and cutting out the ulnar and/or radial upper ends in function of profiles defined by this guide.

It may, in addition, include cutting out the ulna, forming a surface inscribed in a cylinder and centered on a geometric axis of the outer surface of the trial trochlea. In that case, the trial trochlea is advantageously maintained in position with respect to the ulna during cut-out thereof, cut-out being performed, at least in part, around this trial trochlea.

In addition, the ulna may be cut out by means of a bell-shaped saw guided in a member provided with a guiding ring coaxial with the trial trochlea.

Finally, according to an advantageous aspect of this method, the guide is immobilized with respect to the ulna due to three screws passing through a support of the guide and coming respectively into abutment on the olecranon, on the posterior planar triangle and on the lateral plane of the ulna.

BRIEF DESCRIPTION OF THE DRAWINGS

The invention will be more readily understood and other advantages thereof will appear more clearly in light of the following description an embodiment of an ancillary tool in accordance with its principle and of its method of use, given solely by way of example and made with reference to the accompanying drawings, in which.

DESCRIPTION OF THE PREFERRED EMBODIMENT

An ancillary tool 10 according to the invention can be immobilized with respect to an ulna C and to a radius R of an elbow joint to be fitted out with an artificial ulnar component and/or an artificial radial component.

This ancillary tool 10 comprises a plurality of trials of humeral articular assemblies $20_1$, $20_2$ and $20_3$ which, for simplification, are called "trial humeral trochleas," and which a surgeon can compare successively with the anatomical trochlea of the corresponding humerus or install in the sigmoidal cavity of the ulna. Of course, the number of trial humeral trochleas is not limited to three and depends on the precision desired during this comparison.

The trial humeral trochleas $20_1$, $20_2$, $20_3$ are of symmetry of revolution, and each includes a central bore 21 that allows it to be assembled on a support 31 to form a reinforcement of a cut-out guide 30 belonging to the ancillary tool 10.

The support 31 is formed by mechanical assembling of a plurality of metallic pieces. More precisely, the support 31 comprises a U-shaped stirrup element 32 on which is mounted a hollow shaft 33 which may be inserted in the bore 21 of the trial trochlea selected.

It is assumed in the following that trial trochlea $20_2$ has been selected by comparison with the anatomical trochlea.

This trial trochlea $20_2$ is then placed in abutment against the inner surface $S_C$ of the olecranon and the articular surface $S_R$ of the radial head, in a position close to that of the anatomical trochlea before dislocation of the elbow.

The shaft 33 is mounted on a first arm 34 of the stirrup element 32. A second arm 35 of the stirrup element 32 terminates in a ring 36 of which $l_{36}$ denotes the width. The ring 36 and the hollow shaft 33 are coaxial and centered on an axis X-X' which is also the axis of symmetry of the trial trochlea $20_2$ mounted on the support 31.

The support 31 also comprises a tab 37 immobilized on the support 31 and which comprises two arms 37a and 37b substantially perpendicular to each other, the arm 37b comprising at its free end a guide 37c defining a slot 37d substantially parallel to axis X-X'.

Figure 1:
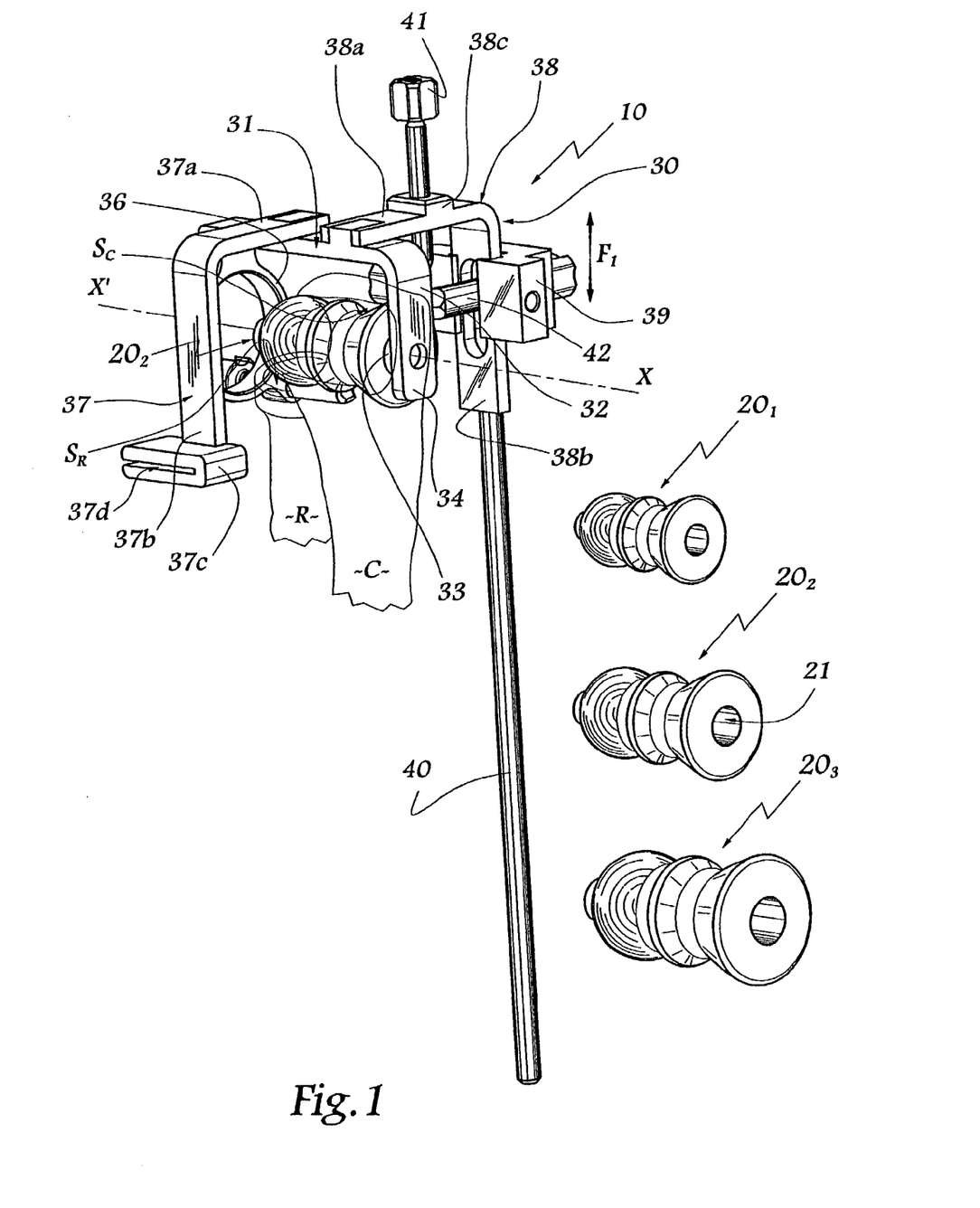
FIG. 1 is a view in perspective of an ancillary tool according to the invention during a first step of use, the ulna and the radius being shown in faint lines in order to render the drawing clearer.

The stirrup element 32 also supports a second tab 38 fixed on the stirrup element 31 and which comprises two arms 38a and 38b substantially perpendicular to each other. The arm 38b is equipped with a carriage 39 secured to a rod 40, the carriage 39 being able to slide with respect to the arm 38b as represented by the double arrow $F_1$ in FIG. 1.

The arm 38a is provided with a boss 38c in which is formed a tapping for receiving a screw 41 intended to come into abutment against the proximal part of the olecranon.

As for the carriage 39, it is equipped with a screw 42 which comes into abutment against the posterior planar triangle of the ulna.

Finally, the ring 36 is provided with an extension 36a in which is screwed a screw 43 intended to come into abutment against the lateral plane of the ulna.

The cut-out guide 30 is placed in position with respect to the ulna C and to the radius R by arranging the rod 40 substantially along a patient's forearm and then by screwing the screws 41 to 43 more or less, causing the trial trochlea $20_2$ to be positioned with respect to the ulnar ($S_C$) and radial ($S_R$) articular surfaces substantially in the same way as the anatomical trochlea when the elbow is not dislocated. When this position is attained, the screws 41 to 43 are screwed, so that the guide 30 is immobilized with respect to the ulna, and therefore with respect to the radius.

Figure 2:
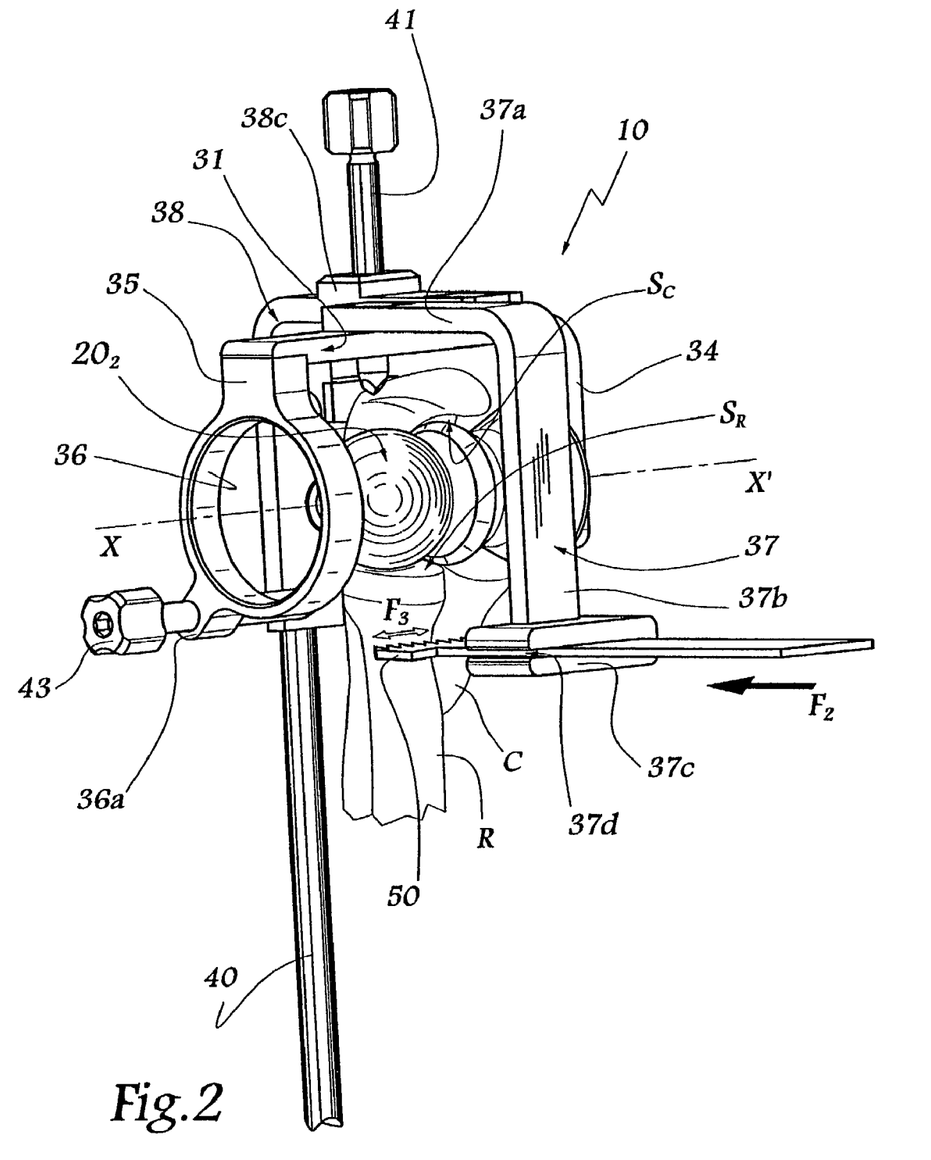
FIG. 2 is a view in perspective of the ancillary tool of FIG. 1, during a second step of use.

In this position and as shown in FIG. 2, it is possible to introduce a blade 50 in the slot 37d so as to cut the upper end of the radius R. The position of the line of cut of the radius R is determined by taking into account the height of the radial knob which will be subsequently positioned on the radius. This guarantees that the articular surface of this radial knob will be correctly positioned with respect to the trochlea with which it must cooperate.

In FIG. 2, arrows $F_2$ and $F_3$ represent the directions of introduction and of reciprocating movement of the blade 50 with a view to cutting out the radius R.

Figure 3:
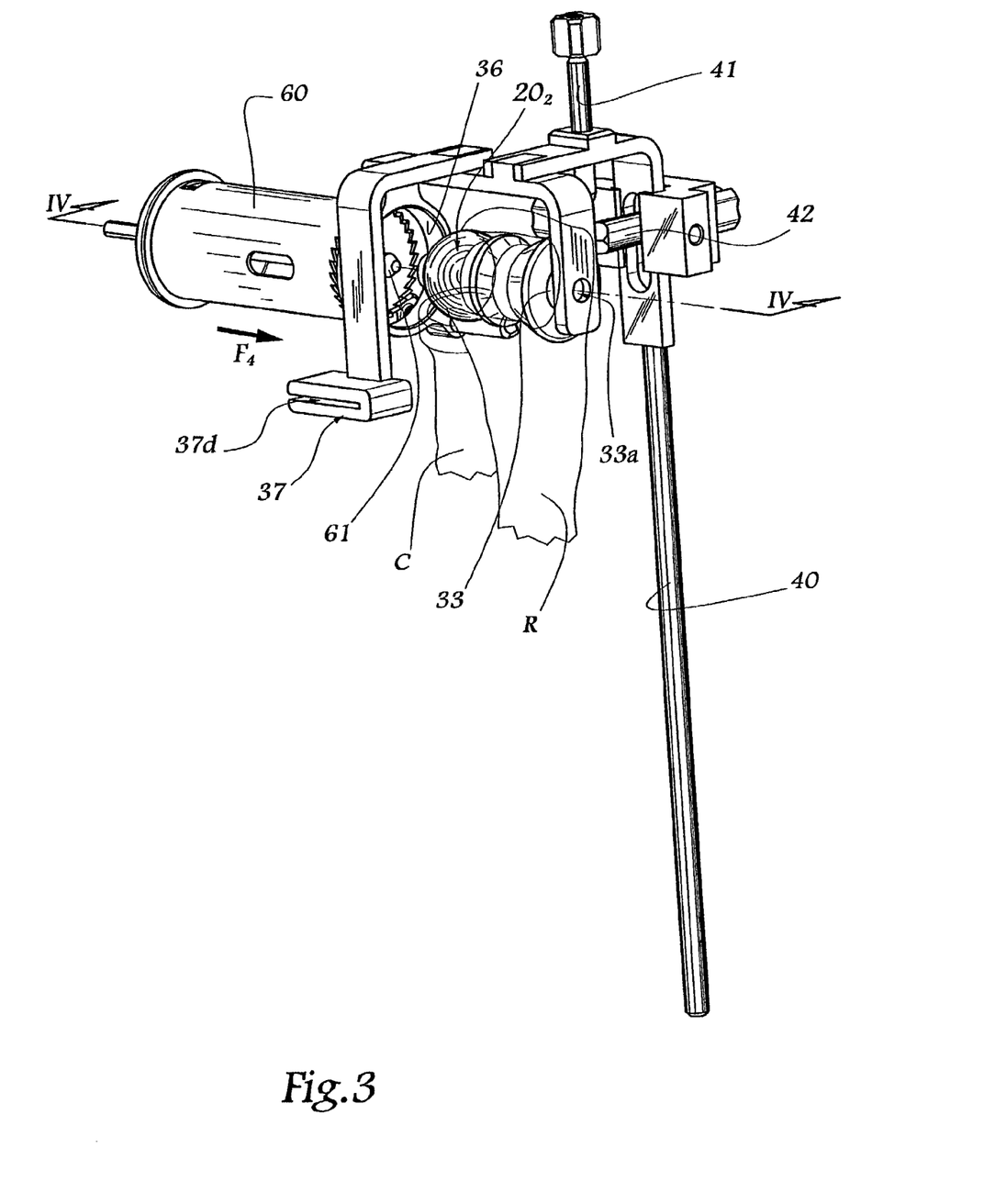
FIG. 3 is a view similar to FIG. 1 during a third step of use.
Figure 4:
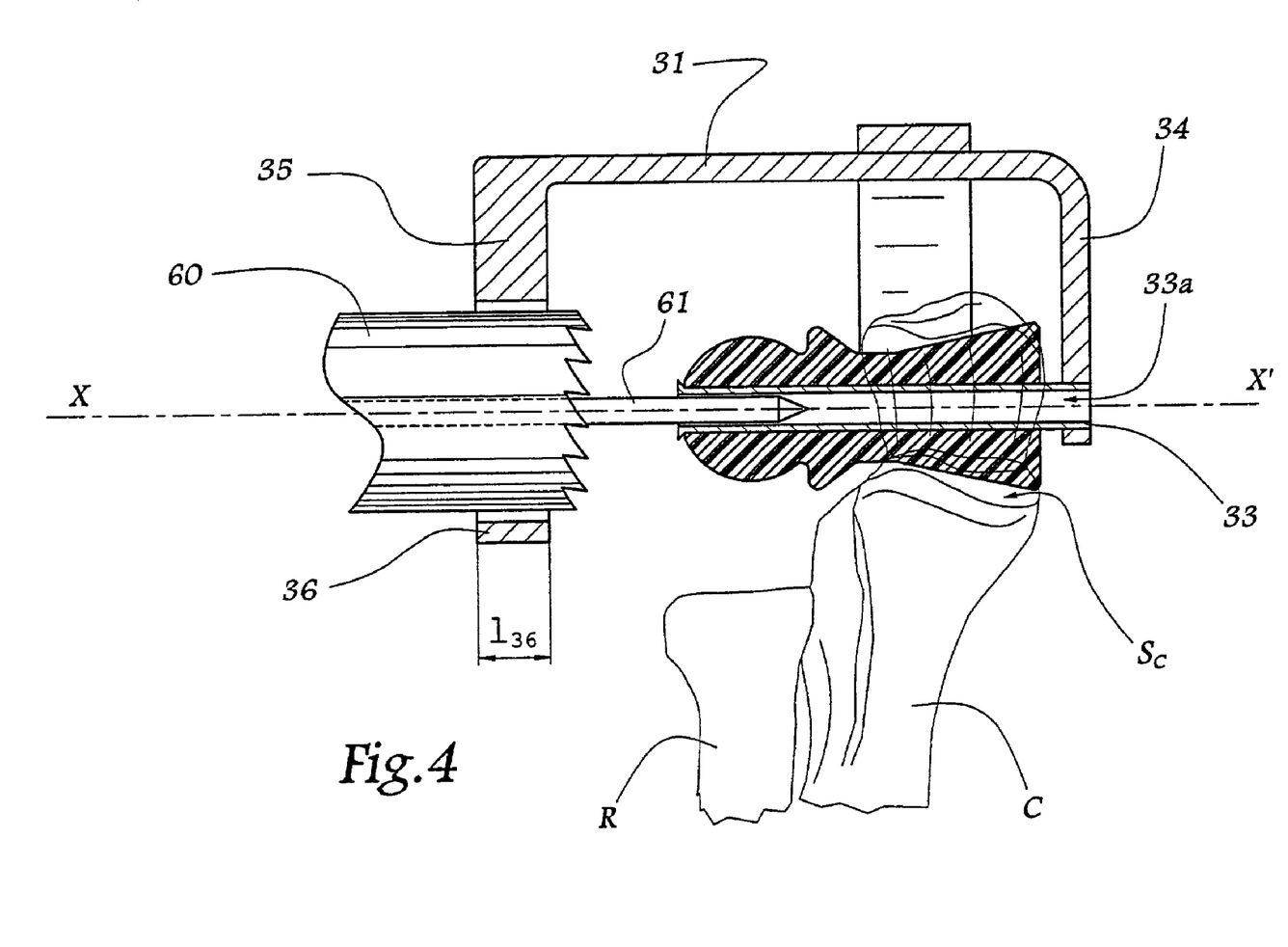
FIG. 4 is a partial section along line IV-IV in FIG. 3.

As is more particularly visible in FIGS. 3 and 4, it is then possible to introduce a bell-shaped saw 60 in the ring 36, parallel to axis X-X' and as represented by arrow $F_4$. The bell-shaped saw 60 is equipped with a central guiding finger 61 aligned on axis X-X' and whose diameter allows it to penetrate in the inner volume 33a of the shaft 33, which makes it possible to efficiently guide the tubular saw 60 in cooperation with the inner bearing surface of the ring 36 which extends over its width $l_{36}$.

Figure 5:
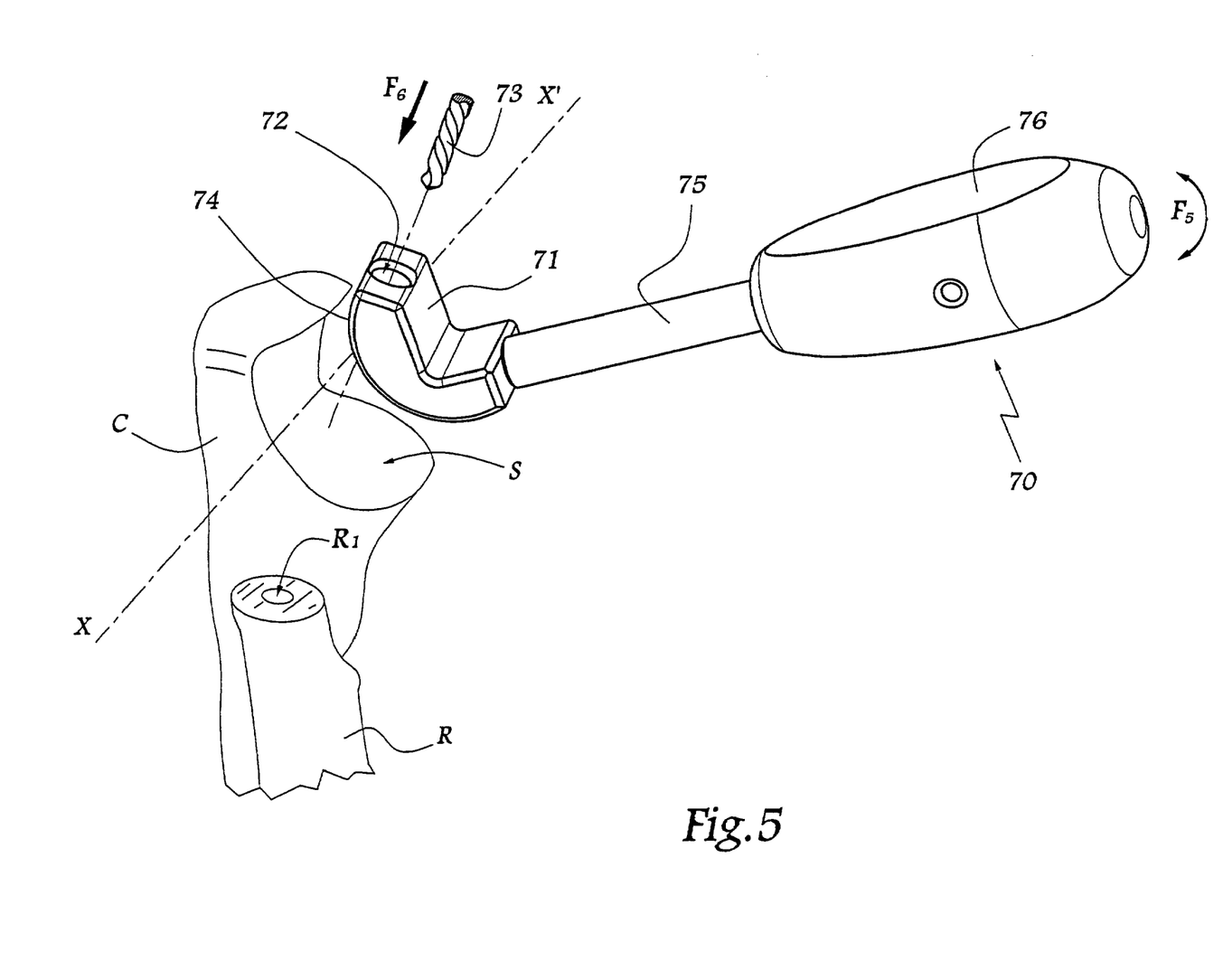
FIG. 5 is a view in perspective of the upper ends of the radius and of the ulna, during a fourth step of use.
Figure 6:
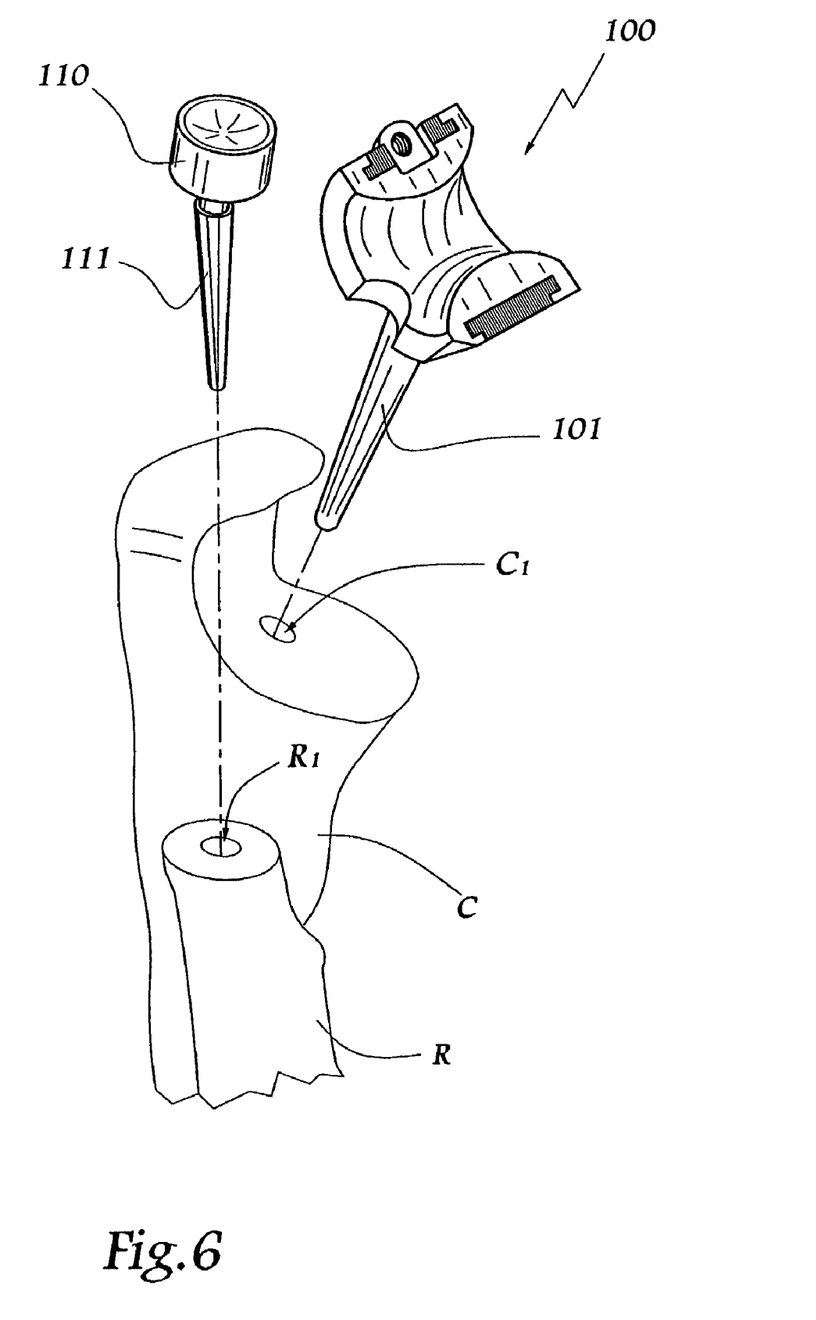
FIG. 6 is a view similar to FIG. 5 during the positioning of artificial components on the ulna and on the radius.

The bell-shaped saw makes it possible to cut out the olecranon of the ulna C around the trial trochlea $20_2$, creating a cylindrical surface portion with circular base S, more particularly visible in FIG. 5.

When the radius and the ulna have been cut out, the cut-out guide 30 is removed by unscrewing screws 41 to 43 and the bones can be prepared for receiving the artificial components.

A bore $R_1$ in the radius R is made substantially along the axis of the neck of the radius, while a guiding tool 70 is used for determining the direction of a bore $C_1$ to be performed in the ulna for receiving an anchoring shank 101 of an artificial ulnar component 100. The tool 70 comprises a template 71 provided with a bore 72 for receiving and guiding a drill 73, a punch or a suitable cut-out tool. An outer surface 74 of the template 71 is a portion of a cylindrical surface with the same radius as the surface S and the template 71 may pivot about axis X-X' which is the axis of symmetry of the surface S.

In order to control the angular positioning of the template 71 with respect to axis X-X', i.e. the direction of the bore 72 with respect to the ulna C, the template 71 is connected by a shaft 75 to a handle 76 intended to be held by the surgeon or one of his/her assistants and allowing an effort of tipping $F_5$ of the template 71 about axis X-X' to be exerted.

It will be understood that, when the template 71 is in contact with the surface S, it is possible to create the bore $C_1$ by introducing the drill 73 in the bone through the bore 72, as schematically represented by arrow $F_6$.

When the bores $C_1$ and $R_1$ have been made, the ulnar component 100 can be positioned by introducing its anchoring shank 101 in the bore $C_1$, while a radial knob 110 can be positioned on the radius R by introducing its anchoring shank 111 in the bore $R_1$.

As a result of the invention, it is possible to position components 100 and 110 correctly. By taking into account the combined anatomy of the ulna C, the radius R, and the humerus as in the configuration of FIG. 1 which determines the positioning of the guide 30 and the cutting zones, the trial humeral trochlea $20_2$ is in abutment on the anatomical articular surfaces of the ulna C and the radius R. This results in a precise positioning of these components, with a correct ligamentary balance of the joint.

The invention has been described for positioning an ulnar component 100 and a radial knob 110, but it may, of course, be used for positioning one of these components only.

The invention has been described for use via a firstly lateral approach, in particular for access of the bell-shaped saw 60 via the lateral side of the joint. A firstly medial approach may, of course, be used, with an ancillary tool designed symmetrically with respect to that shown in the Figures.

The invention claimed is:

1. An ancillary tool for implanting an elbow prosthesis in a patient, the tool comprising:
at least one trial distal humeral trochlea with a shape representative of at least a portion of an anatomical distal humeral trochlea of the patient, the trial distal humeral trochlea adapted for temporary engagement with proximal anatomical articular surfaces of an ulna and a radius without requiring resection of the anatomical distal humeral trochlea;
a guide attached to the trial distal humeral trochlea temporarily engageable with the proximal anatomical articular surfaces of the ulna and the radius, and at least one of the ulna or the radius, wherein the guide comprises a U-shaped support having a first leg and a second leg for mounting the trial distal humeral trochlea such that a central axis of the trial distal humeral trochlea is coaxial with an axis extending from the first leg to the second leg; and
at least one cutting guide adapted to prepare at least a proximal end of the ulna or a proximal end of the radius to receive at least one of a proximal ulnar component or a proximal radial component, respectively.

2. The ancillary tool of claim 1 wherein the trial humeral trochlea is adapted to temporarily engage with an inner surface of an olecranon on the ulna.

3. The ancillary tool of claim 1 wherein the trial humeral trochlea is adapted to temporarily engage with the articular surface of a radial head.

4. The ancillary tool of claim 1 comprising a plurality of trial humeral trochlea.

5. The ancillary tool of claim 1 wherein the trial humeral trochlea is symmetrical around a central axis.

6. The ancillary tool of claim 1 wherein the trial humeral trochlea comprises a three-dimensional surface corresponding generally to the anatomical distal humeral trochlea.

7. The ancillary tool of claim 1 comprising:
a central bore in the trial humeral trochlea; and
at least one cylindrical blade adapted to cut the ulna around the trial humeral trochlea; and
a projection located along a central axis of the cylindrical blade adapted to engage with the central bore during cutting of the ulna.

8. The ancillary tool of claim 1 wherein the guide comprises a shaft adapted to engage with a central bore in the trial humeral trochlea.

9. The ancillary tool of claim 1 wherein the guide comprises a screw adapted to abut against a proximal part of an olecranon on the ulna.

10. The ancillary tool of claim 1 wherein the guide comprises a screw adapted to abut against a posterior planar triangle of the ulna.

11. The ancillary tool of claim 1 wherein the guide comprises a screw adapted to abut against a lateral plane of the ulna.

12. The ancillary tool of claim 1 wherein the guide comprises a securing structure adapted to immobilize the guide with respect to the ulna.

13. The ancillary tool of claim 1 wherein the cutter is a blade and the cutting guide comprises at least one slot adapted to guide the blade to resect a proximal end of the radius.

14. The ancillary tool of claim 1 wherein the cutting guide comprises at least one circular opening adapted to guide a blade to resect the ulna.

15. The ancillary tool of claim 1 wherein the cutting guide comprises at least one circular opening adapted to guide a cylindrical blade to prepare a cylindrical surface on the ulna.

16. The ancillary tool of claim 1 wherein the cutting guide comprises at least one circular cutting guide with an axis of symmetry co-linear with an axis of symmetry of the trial humeral trochlea.

17. The ancillary tool of claim 1, wherein the cutter includes at least one cylindrical blade adapted to cut a circular surface in an olecranon of the ulna around the trial humeral trochlea.

18. The ancillary tool of claim 1 comprising a rod adapted to be positioned parallel to a patient's fore-arm.

19. The ancillary tool of claim 1 wherein the tool is adapted for use with a total elbow prosthesis or a partial elbow prosthesis.

20. The ancillary tool of claim 1 wherein the tool is adapted for at least one of a lateral approach or a medial approach.

21. A kit for an elbow prosthesis comprising:
the ancillary tool of claim 1; and
a proximal ulnar component.

22. A kit for an elbow prosthesis comprising:
the ancillary tool of claim 1; and
a proximal radial component.

23. An ancillary tool for implanting an elbow prosthesis in a patient, the tool comprising:
a plurality of trial distal humeral trochlea with a shape representative of at least a portion of an anatomical distal humeral trochlea of the patient, each of the trial distal humeral trochlea is adaptable for temporary engagement with proximal anatomical articular surfaces of an ulna and a radius without requiring resection of the anatomical distal humeral trochlea;
at least one cutting guide attached to the trial distal humeral trochlea temporarily engagable with the proximal anatomical articular surfaces of the ulna and the radius, and at least one of the ulna or the radius, the at least one cutting guide having at least one circular cutting guide with an axis of symmetry co-linear with an axis of symmetry of the trial humeral trochlea and adapted to prepare at least a proximal end of the ulna or a proximal end of the radius while taking into account the combined anatomy at the intersection of the ulna, the radius and the humerus.

24. An ancillary tool for implanting an elbow prosthesis in a patient, the tool comprising:
at least one trial distal humeral trochlea with a shape representative of at least a portion of an anatomical distal humeral trochlea of the patient, the trial distal humeral trochlea is adapted for temporary engagement with proximal anatomical articular surfaces of an ulna and a radius without requiring resection of the anatomical distal humeral trochlea;

a guide including a support having a first leg, a second leg terminating in a ring and a third leg connecting the first leg and the second leg, and a tab extending from the third leg and having a first arm and a second arm, wherein the second arm is substantially perpendicular to the first arm, and wherein the guide is adapted to be positioned with respect to the trial distal humeral trochlea, and at least one of the ulna or the radius;

at least one cutting guide adapted to prepare at least a proximal end of the ulna or a proximal end of the radius to receive at least one of a proximal ulnar component or a proximal radial component; and a securing structure adapted to immobilize the guide with respect to the ulna.

25. An ancillary tool for implant an elbow prosthesis in a patient, the tool comprising:

a trial humeral trochlea having a shape corresponding to an anatomical humeral trochlea of the patient such that the trial humeral trochlea is configured to abut anatomical articular surfaces of an ulna and a radius of the patient;

a guide attached to the trial humeral trochlea , the guide including,
 a first leg maintaining the trial humeral trochlea; and
 a second leg; wherein, a central axis of the trial humeral trochlea is coaxial with an axis extending from the first leg to the second leg;

at least one cutting guide maintained by the second leg; and a cutter received in the cutting guide such that the cutter is positioned for cutting at least one of a proximal end of the ulna or a proximal end of the radius while the trial humeral trochlea is abutted with the anatomical articular surfaces of the ulna and radius.

* * * * *

UNITED STATES PATENT AND TRADEMARK OFFICE
CERTIFICATE OF CORRECTION

| | | |
|---|---|---|
| PATENT NO. | : 7,922,728 B2 | Page 1 of 1 |
| APPLICATION NO. | : 10/189378 | |
| DATED | : April 12, 2011 | |
| INVENTOR(S) | : Alain Tornier et al. | |

It is certified that error appears in the above-identified patent and that said Letters Patent is hereby corrected as shown below:

Column 7

<u>Line 19</u>

Replace the word "implant" with -- implanting --

Signed and Sealed this
Twenty-fourth Day of July, 2012

David J. Kappos
*Director of the United States Patent and Trademark Office*